US007231331B2

(12) United States Patent
Davis

(10) Patent No.: US 7,231,331 B2
(45) Date of Patent: *Jun. 12, 2007

(54) METHOD AND SYSTEM TO DETECT STRESS CORROSION CRACKING IN PIPELINE SYSTEMS

(75) Inventor: James D. Davis, Beaumont, TX (US)

(73) Assignee: Kinder Morgan, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/302,935

(22) Filed: Dec. 14, 2005

(65) Prior Publication Data

US 2006/0100834 A1      May 11, 2006

Related U.S. Application Data

(63) Continuation of application No. 09/906,457, filed on Jul. 16, 2001, now Pat. No. 7,013,249.

(51) Int. Cl.
| G06F 7/60 | (2006.01) |
| G01S 15/00 | (2006.01) |
| F16L 55/44 | (2006.01) |
| G01N 19/08 | (2006.01) |
| G01C 9/00 | (2006.01) |
| G21C 17/00 | (2006.01) |

(52) U.S. Cl. .................. 703/2; 367/115; 405/184.3; 376/249; 73/799; 702/150

(58) Field of Classification Search .................. 703/2; 367/115; 405/184.3; 376/249; 73/799; 702/150

See application file for complete search history.

(56) References Cited

U.S. PATENT DOCUMENTS

| 3,762,446 A | 10/1973 | Tungseth et al. |
| 4,241,430 A | 12/1980 | Kayem et al. |
| 4,507,019 A | 3/1985 | Thompson |
| 5,323,429 A | 6/1994 | Roarty et al. |
| 5,526,689 A | 6/1996 | Coulter et al. |
| 5,571,955 A | 11/1996 | Beavers et al. |
| 5,728,943 A | 3/1998 | Coulter et al. |
| 5,883,311 A | 3/1999 | Hettiarachchi et al. |
| 5,883,815 A | 3/1999 | Drakulich et al. |
| 6,107,811 A | 8/2000 | Caudill et al. |
| 6,155,292 A | 12/2000 | Kurata |
| 6,243,657 B1 | 6/2001 | Tuck et al. |

OTHER PUBLICATIONS

Marr, et al., "Procedures Guide Prediction, Evaluation of Stress Corrosion", Corrosion and Pipe Protection, vol. 81, No. 3, Mar. 1988.

Czyz, et al., "Multi-Pipeline Geographical Information System Based on High Accuracy Inertial Surveys", Proceedings of IPC 2000 International Pipeline Conf., Oct. 2000.

Leeds, et al., "Modified Analysis Method Helps Coating Fault, Pipe Assessment", Corrosion and Pipe Protection, vol. 83, No. 3, Mar. 2000.

Leis, et al., "Stress Corrosion Cracking On Gas Transmission Pipelines, History, Causes and Mitigation", First International Business Conf., Berlin, Dec. 1997.

*Primary Examiner*—Anthony Knight
*Assistant Examiner*—Tom Stevens
(74) *Attorney, Agent, or Firm*—Bracewell & Giuliani, LLP

(57) ABSTRACT

A method for predicting the location of stress corrosion cracking in a steel gas pipeline in which in-line stress corrosion cracking smart tool data, external low level metal loss data and soil characterization data are compiled to predict the location of stress corrosion cracking in a steel gas pipeline segment.

25 Claims, 5 Drawing Sheets

METHOD AND SYSTEM TO DETECT STRESS CORROSION CRACKING IN PIPELINE SYSTEMS

This is a continuation patent application which claims priority to and the benefit of U.S. application Ser. No. 09/906,457, issued U.S. Pat. No. 7,013,249, which was filed on Jul. 16, 2001 and titled *Method for Detecting Near Neutral/Low Ph Stress Corrosion Cracking in Steel Gas Pipeline Systems,* which is incorporated herein in its entirety.

BACKGROUND OF THE INVENTION

1. Technical Field

The present invention relates in general to a method for detecting stress corrosion cracking in steel gas pipelines, and in particular to a method for predicting with a high degree of accuracy the presence at a specific location of stress corrosion cracking in such pipelines.

2. Description of the Prior Art

Since the early 1960's pipe manufacturers have developed high strength steels for pipeline applications in order to reduce the pipe wall thickness required to achieve maximum allowable operating pressures specified by pipeline operators. These higher strength steels have higher tensile or residual stresses and in combination with applied stresses (hoop stresses from pressure generated by compressing natural gas for transportation) increase the potential for stress corrosion cracking (SCC) to occur.

In-line inspection tools or instrumented tools also known as intelligent or smart tools contain various sensors, sophisticated electronics, onboard computers and recording devices that collect data which is later analyzed by a specialist using special software to reveal information about the condition of the pipeline. Technology has been commercially developed and applied to detect pipe body wall metal loss and crack-like features. Unfortunately, the most useful signature from these tools has been ignored. Low level analysis for metal loss has not been used to indicate disbanded coating in conjunction with topography and SCC indications. This methodology is critical to determining where SCC really exists and for prevention of very costly exploratory digs on high-pressure pipeline systems. These are different types of technology with the in-line inspection smart tools run separately to collect the metal loss or crack feature data.

The principles of magnetic flux leakage technology are predominantly used to detect pipe body wall loss in gas pipelines. When the pipe is magnetized to an optimum inspection level and no defects exist, all lines of magnetic flux will be contained within the pipe wall. If defects exist, the lines of magnetic flux will be redistributed around the defect. The result will be that some of the lines of magnetic flux will 'leak' out into the surrounding medium. A magnetic field sensor, scanning along the surface of the pipe wall will detect any leakage field and output an electrical signal proportional to the defect's depth and shape. Originally, analog smart tools were developed using flux leakage technology in the 1960's and presently these tools are being converted to digital technology. Trained analysts review the processed data in a visual computer format to review and interpret the inspection data and grade the metal loss severity. In-line inspection metal loss smart tool vendors typically report the metal loss depth from 15% or greater depth penetration allowing for pipe manufacturing mill tolerance variances. Surveys can be graded at a specific depth more or less than 15% if requested by the operating company and if feasible for the vendor to interpret data results.

The principles of ultrasonic technology have been used successfully by commercial smart tool vendors for many years to find crack-like features in pipeline steels. Ultrasonic waves, such as elastic waves or electromagnetic acoustic waves, are transmitted via transducers into the pipe wall. These waves are reflected when they encounter discontinuities such as cracks and a portion of their energy is reflected back as an ultrasonic signal. The signal is then processed and recorded for later analysis. A serious problem with using ultrasonic technology for finding crack-like features is the inability to adequately distinguish a crack-like feature to non-critical reflector features such as manufacturing inclusions or mechanical scratches on the pipe surface as a result of construction or manufacturing practices. As many as 50% of the crack-like features reported from the smart tool can be attributed to mechanical or metallurgical defects rather than SCC. Interpretation analysts using specially developed computer software grade the survey and prepare the survey report.

Soil characterization and modeling is a tool which predicts SCC susceptibility based on a database of soil characteristics and then combining that information with the physical pipeline characteristics such as steel grade, age, coating type and condition, operating pressure, etc. The soil characterization survey is performed by walking the length of the pipeline segment and periodically collecting a soil sample from pipeline depth with a hand auger. The soil type is determined along with the associated drainage and topography. The bottom soil sample collected at pipeline depth can be tested for pH and presence of carbonate substances and other chemicals known to be present where SCC has been found on pipelines. All data collected is then associated with the pipeline footage/chainage survey. This data is then combined with the pipeline physical characteristics into a specialized computer model to predict the possibility of SCC being present assuming the coating is disbonded allowing the environment to make contact with the pipe wall at the pipeline footage/chainage location.

A hydrostatic test is a method of confirming pipeline integrity by pressuring the pipeline up to a defined pressure above the operating pressure using a liquid medium such as water. For a gas pipeline, it involves removing the pipeline from gas service, installing special test manifolds, filling and pressurizing the pipe using a liquid medium. This technique will find SCC features that will not sustain the achieved pressure, but will not find or identify the location of any sub-critical crack-like features.

Historically, gas pipeline operators have relied on periodically pressure testing pipelines to confirm integrity as a method of finding SCC. Some operators have also run in-line inspection SCC smart tools to identify where the cracks could be located. Unfortunately, numerous excavations have to be performed where mechanical or metallurgical false reflector indications are found rather than SCC. Other operators have used the soil characterization and SCC model surveys to perform excavations to investigate whether SCC is present. The soil characterization survey does not provide a survey that definitively confirms SCC but indicates the possible presence if the coating is disbanded and the environment has come into contact with the pipeline for a sustained period of time to promote crack growth.

Stress corrosion cracking is a form of environmentally assisted cracking where the surrounding environment, pipe material and stress act together to reduce the strength or load carrying capacity of the pipeline. It is the result of a chemistry and a physics problem working together, and the mechanism is electrochemical-mechanical. When steel comes into contact with water, the minerals and gases in the water at the pipe surface create cells that attack the steel. This chemical or electrochemical reaction is corrosion and, in other situations, would typically create general pipe wall thinning or pits in the steel. In SCC, stress and corrosion work together to weaken the pipe. Ultimately, the cracks continue to develop in depth and width or merge together with adjacent cracks to make a single longer crack to the point that the crack location is weakened beyond the stress load and thus mechanical failure occurs.

Research into the process of near neutral/low pH stress corrosion cracking has only been initiated in the last fifteen years or so since the first pipeline failure occurred that was attributed to this type of SCC. The scientific research community generally agrees that the following processes are required for near neutral or low pH SCC to develop.

Three conditions are necessary and must be present for stress corrosion cracking to occur: 1) a chemical environment that initiates a crack at the pipeline wall surface; 2) a susceptible steel pipe material, and 3) tensile stress in the pipeline steel. If any one of these three conditions listed above could be eliminated or reduced to a point where cracking would not occur, then SCC could be prevented.

Cracks are most likely initiated at pits on the steel surface of the pipeline where a localized environment is generated that has a pH low enough to produce atomic hydrogen in the pit. The presence of carbon dioxide in the groundwater assists in creating near neutral pH levels. Some of the discharged atomic hydrogen enters the steel, degrading the mechanical properties locally so that the cracks are initiated or grown by a combination of dissolution and hydrogen embrittlement. Continued anodic dissolution in the crack is necessary for crack growth, assisted by hydrogen entry into the steel. The plastic stress level necessary to produce cracking may not be related solely to fracturing the embrittled steel. It may also contribute by rupturing the protective film, allowing hydrogen to reach and then penetrate the steel. The cracks generated by near neutral/low pH SCC are generally transgranular where the cracks follow a path across or through the grains.

Near neutral/low pH stress corrosion cracking is associated with shallow external corrosion pitting. Internal in-line inspection smart tools are commercially available that detect external corrosion pitting. The environment for near neutral/low pH SCC can only develop after damage to or disbondment of the pipe coating and in the absence of the cathodic protection current used to control external pipeline corrosion. Some types of pipeline coatings when disbanded act as a barrier shielding cathodic protection from reaching the pipe surface.

The Canadian National Energy Board held an inquiry and subsequently published a Report of the Inquiry titled Stress Corrosion Cracking on Canadian Oil and Gas Pipelines in November 1996. Following that report the Canadian Energy Pipeline Association (CEPA) published Stress Corrosion Cracking Recommended Practices in May 1997. These documents discuss the processes described above (in-line metal loss and SCC smart tools, soil characterization and modeling) as separate technologies. The CEPA SCC Recommended Practices consist of a compilation of guidelines based on practices at the time of publication to support companies in the management of their longitudinal, low-pH SCC concerns. In April 1995, the Gas Research Institute published a report for member companies titled Stress Corrosion Cracks in Pipelines: Characteristics and Detection Considerations. This report presents an overview of stress corrosion cracking in pipelines with a particular emphasis on aspects that are relevant to the development of in-line inspection tools and interpretation of inspection signals. Numerous other research articles on near neutral/low pH SCC mechanics have been written and published by the National Association of Corrosion Engineers.

There are many disadvantages associated with the traditional SCC detection methods for near neutral/low pH stress corrosion cracking on steel gas pipelines. The traditional SCC detection methods include using separately 1) in-line pipeline inspection data obtained with smart tools that are designed to detect external pipeline wall crack-like features; 2) in-line smart tool inspection for external metal loss corrosion anomalies; or 3) soil characterization surveys having computerized data modeling to determine susceptible terrain for SCC.

One disadvantage is that the traditional near neutral/low pH SCC detection methods yield false or inconclusive results. Moreover, the methods to confirm the location of SCC in a pipeline are costly and highly labor-intensive. Heretofore, such pipelines in which SCC was suspected were taken out of gas transmission service, and subjected to hydrostatic testing.

Another disadvantage is that the results of the traditional SCC detection methods have not been integrated and comparatively evaluated to determine with high confidence whether actual SCC exists at a physical gas pipeline location. A key component not used before this invention was to utilize low level analysis of metal loss in-line inspection tool surveys rather than conventional grading methodology. Heretofore, such detection results were evaluated separately.

Accordingly, prior to the development of the present invention, there has not been a method of integrating in-line pipeline wall inspection results, in-line low level external metal loss external corrosion analysis results and soil characterization model results to determine with high confidence whether actual SCC exists at a physical gas pipeline segment location. Therefore, the art has sought a low cost and reliable method of integrating such methods to confirm and/or predict the location of segment of a steel gas pipeline that is susceptible to SCC.

SUMMARY OF INVENTION

In accordance with the invention, the foregoing advantages have been achieved through the present method for predicting the location of stress corrosion cracking in a steel gas pipeline in which stress corrosion cracking smart tool data, external low level metal loss data and soil characterization data are compiled for a steel gas pipeline segment. At least two, but preferably three technologies are merged together and preferably evaluated simultaneously to predict with a high degree of accuracy the location of stress corrosion cracking in a steel gas pipeline segment.

DETAILED DESCRIPTION OF PREFERRED EMBODIMENT

This invention details a method of detecting near neutral/low pH stress corrosion cracking in pipeline steels using three separate pipeline investigation techniques. Near neutral/low pH stress corrosion cracking occurs in pipeline steels when a limited set of conditions are met. These conditions include the pipe having residual or inherent tensile stress applied to the pipe outer surface, disbonded external pipe coating allowing a thin film of water between the pipe and coating, and soil environmental and drainage topography conditions that are conducive to developing stress corrosion cracking.

Figure 1:
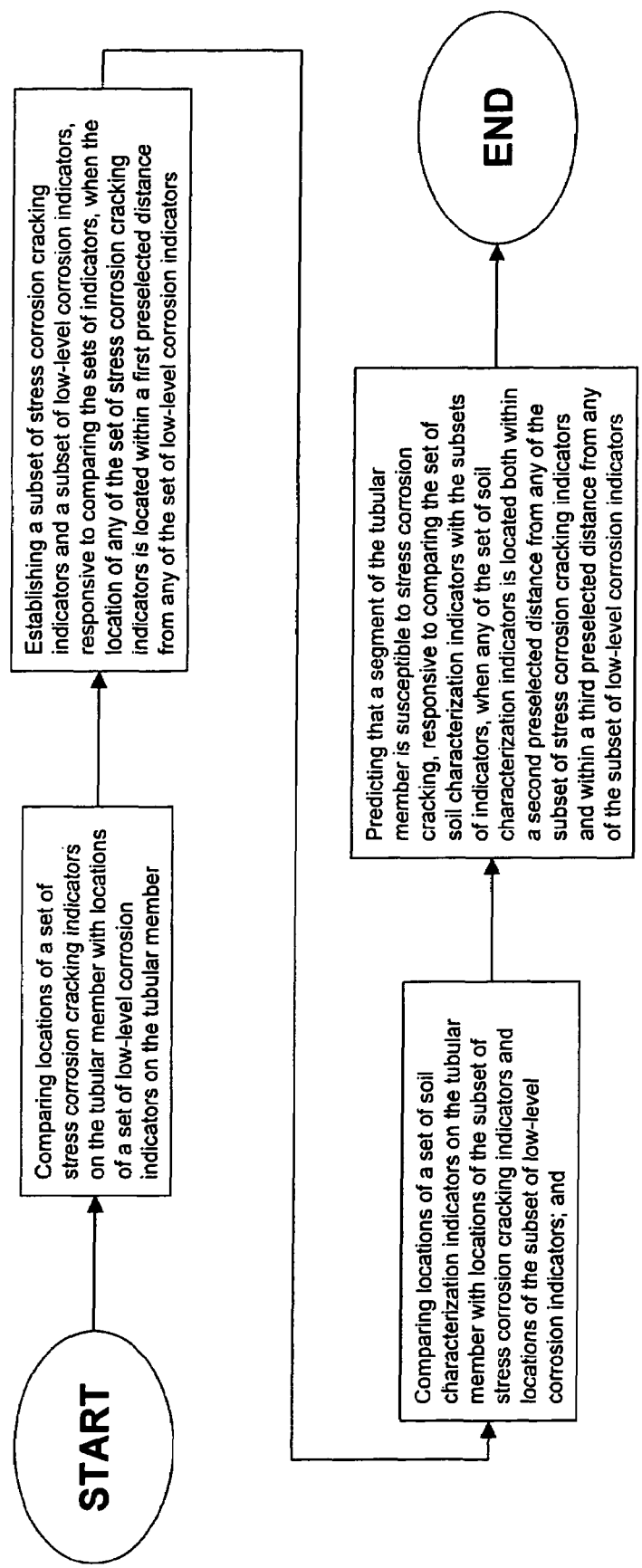
FIG. 1 is a flow diagram of a method for determining crack locations on a tubular member, in accordance with an embodiment of the present invention.
Figure 2:
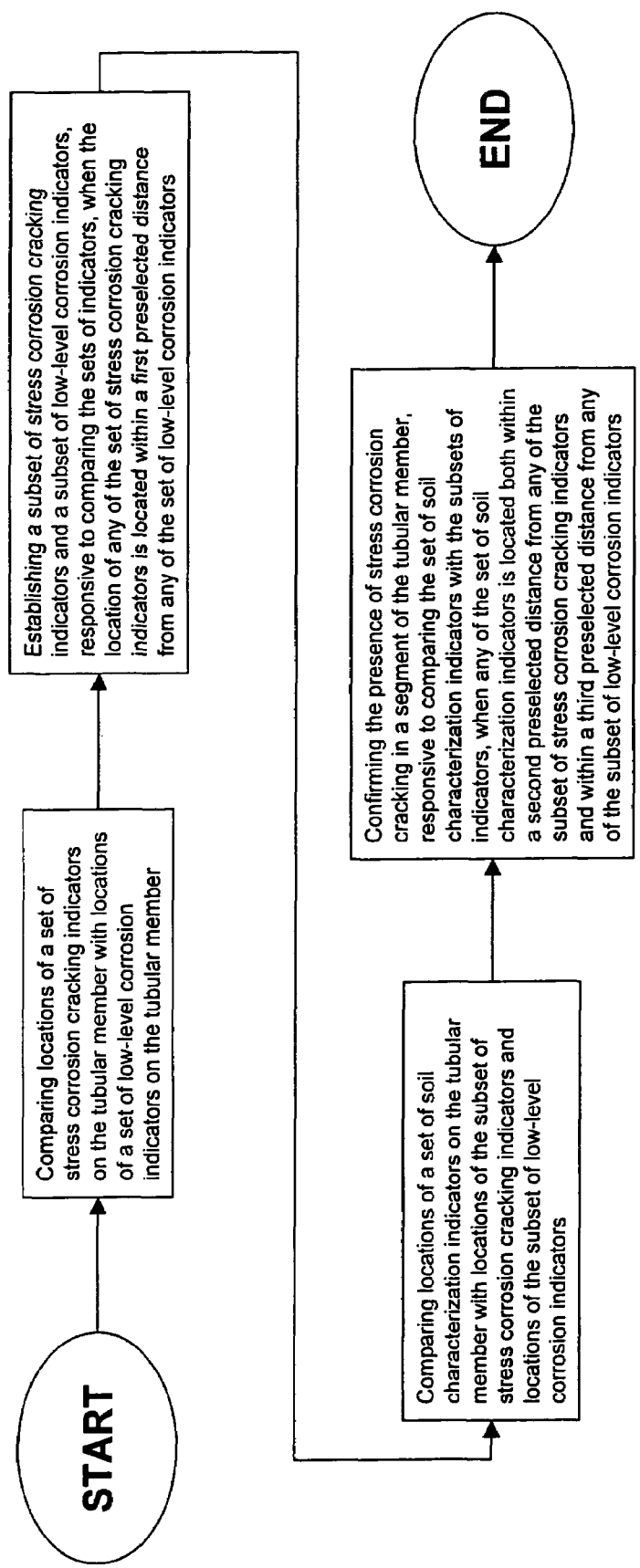
FIG. 2 is a flow diagram of a method for determining crack locations on a tubular member, in accordance with an embodiment of the present invention.
Figure 3:
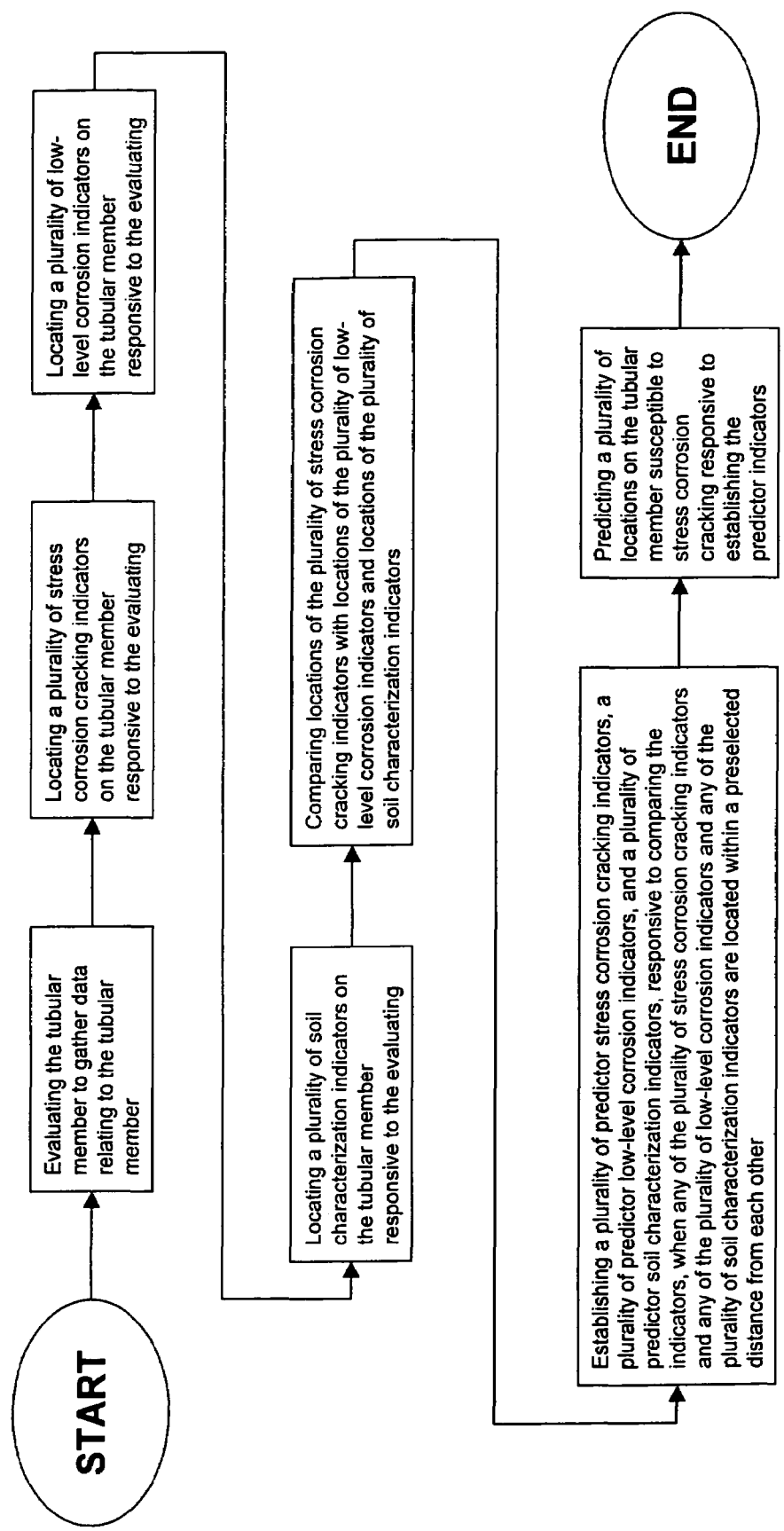
FIG. 3 is a flow diagram of a method for determining crack locations on a tubular member, in accordance with an embodiment of the present invention.
Figure 4:
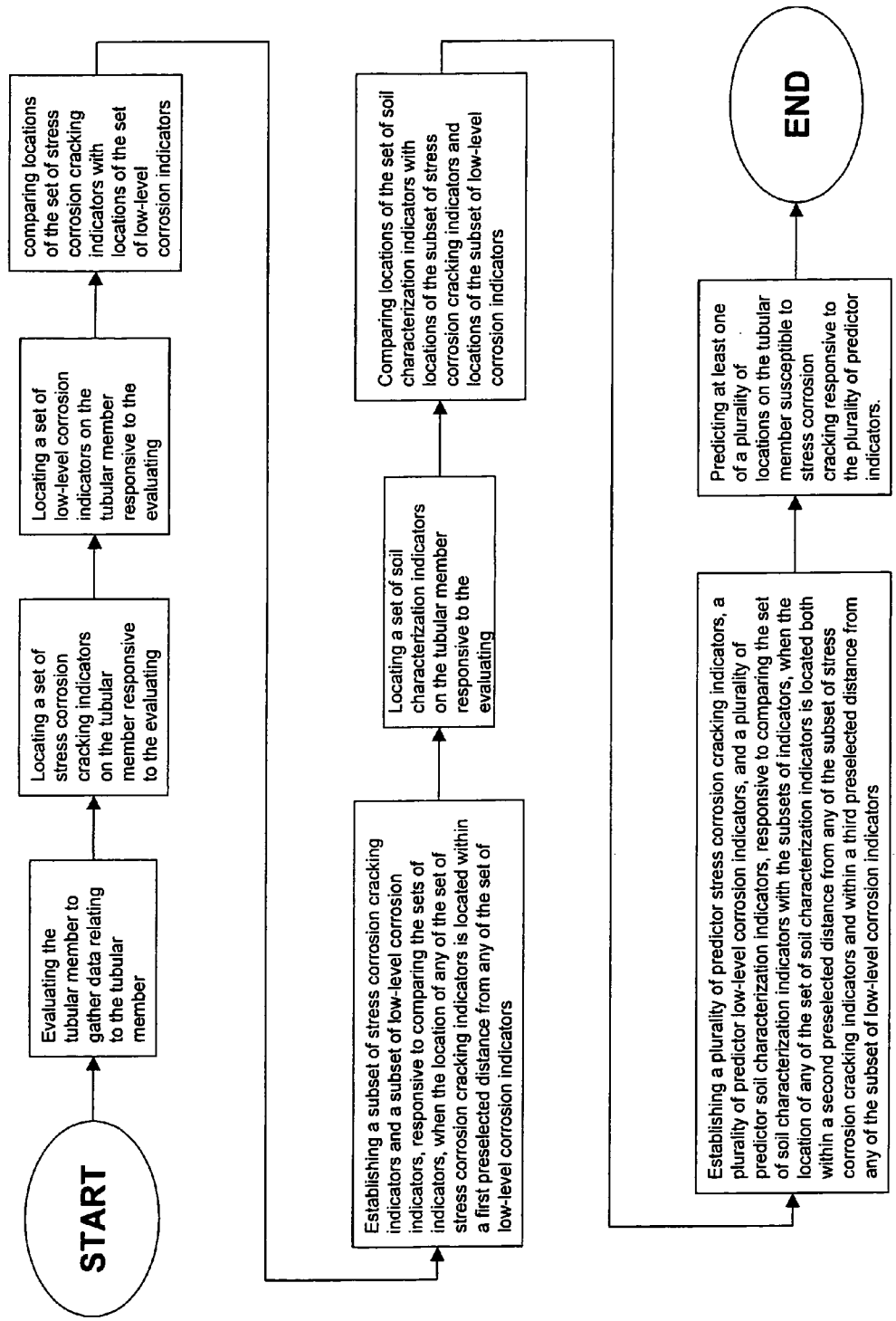
FIG. 4 is a flow diagram of a method for determining crack locations on a tubular member, in accordance with an embodiment of the present invention.
Figure 5:
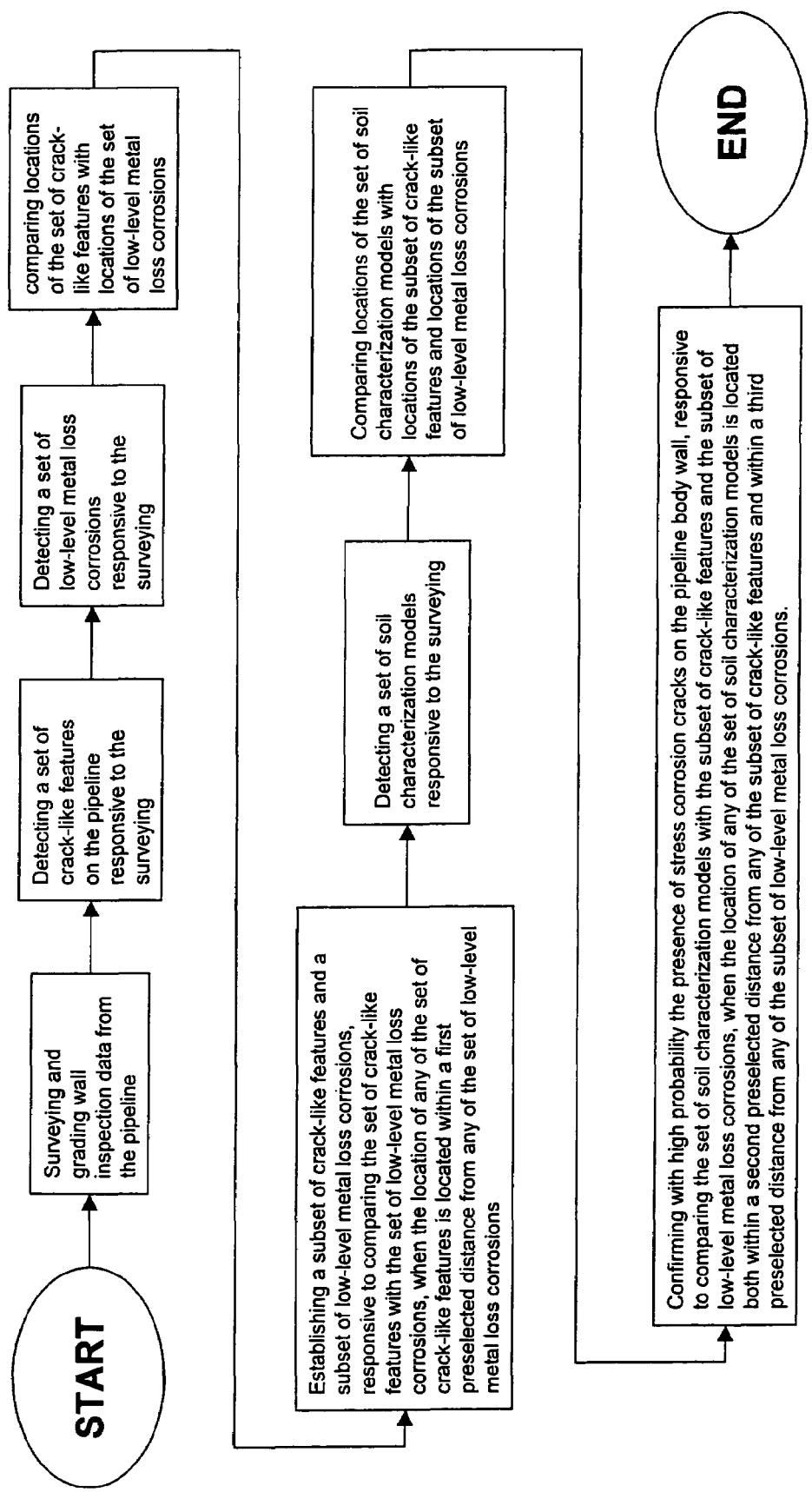
FIG. 5 is a flow diagram of a method for determining crack locations on a tubular member, in accordance with an embodiment of the present invention.

Referring now to FIGS. 1–5, the method for predicting the location of stress corrosion cracking in a steel gas pipeline of this invention includes the steps of 1) compiling stress corrosion cracking smart tool data on a segment of a steel gas pipeline; 2) compiling external low level metal loss data on the steel gas pipeline segment at or near the stress corrosion cracking feature; 3) compiling soil characterization data in the terrain near the steel gas pipeline segment; and 4) matching at least two, preferably the three technologies to predict the presence of stress corrosion cracking in the steel gas pipeline segment.

This method brings together separately available technologies to confirm the likelihood of SCC on a steel pipeline. Pipeline wall inspection data which show crack-like indications or features from an in-line SCC smart tool, expanded low level metal loss from a separate in-line smart tool, and soil chemistry and terrain data from soil characterization surveys are empirically compared and/or matched to indicate whether near neutral/low pH stress corrosion cracking could be present in a given steel gas pipeline segment.

A SCC in-line inspection smart tool survey report for pipeline wall data is performed by a vendor. The inspection uses elastic wave (EW) technology or other transverse wave technology such as electro-magnetic acoustic technology (EMAT) to detect crack-like features, often referred to as EW reflectors or EMAT reflectors, respectively. The vendor then grades the report and publishes the location where these features have been detected on the pipe body wall. The features detected, however, include false crack-like reflectors, such as lamination, slivers, inclusions, or surface scratches from the mill or pipeline construction activities that the in-line smart tool vendor cannot distinguish from SCC.

The in-line external metal loss inspection survey is also performed by a vendor. This survey is performed and graded by the vendor to identify low level external metal loss corrosion, typically using digital magnetic flux leakage technology. This survey is graded by the vendor to include external corrosion anomalies from the smallest detectable indication in percent of wall loss, up to 10 to 15 percent wall thickness loss. This information provides the pipeline operator a confirmation that the pipeline coating has disbanded in the immediate area, allowing the soil/water environment to intrude between the coating and pipe wall which results in corrosion pitting. Corrosion plays an important part in the initiation of near neutral/low pH stress corrosion cracks. A corrosion pit, trench, or other discontinuity on the pipe surface acts as a stress riser. The low level external corrosion metal loss analysis by the in-line inspection smart tool vendor confirms shallow corrosion pitting and disbonded coating at the immediate footage/chainage and pipe body wall circumference orientation. Heretofore, it has not been known to grade surveys for this low-level external metal loss.

Comparing the SCC crack feature location with the low level external metal loss analysis confirms whether shallow pitting and disbonded coating exist in the immediate physical location and orientation of the reported crack feature. The probable presence of stress corrosion cracking is also confirmed if the soil characterization survey/model matches the location as susceptible to crack development. Matching the crack-like feature, low level external metal loss presence, and soil characterization model SCC susceptibility to a pipe body wall location confirms with high probability the presence of stress corrosion cracks rather than other manufacturing or pipeline construction anomalies.

Preferred embodiments of this invention are further described by the following examples.

EXAMPLE 1

An in-line inspection revealed a crack-like feature in a steel gas pipeline segment located at an absolute distance of 99481.2 ft from pipeline launch, as shown in line 1 of Table I, below. The orientation of the feature was 5:42 on a 12-hour clock. The axial length (relative longitudinal distance) was 7.3 inches. The peak depth of the feature was 30% of pipeline wall thickness where nominal pipeline wall thickness was 0.297 inches. The feature detected (EW reflector) was detected in the pipe body region. Additional reflectors within this pipe joint segment were located, and such features should also be examined by non-destructive testing if this segment is accessible. Low level external metal loss has been identified within this pipeline segment. The location of this crack like feature (EW reflector) matched with an area of low level external metal loss. Also, the soil and terrain data was graded as being SCC susceptible, category AL1. The graded SCC susceptible categories are AL1 through AL7. The "A" means that the pipeline is coated with asphalt enamel. The "L" means that the soil is graded as having near neutral or low level pH. The last digit is a soil environment description code number, with 1 indicating glaciofluvial (sandy and/or gravel textured) and other numbers representing various types of soil environments. The girth weld at the upstream end of the feature spool is 28600. The location of this weld is 1367.5 ft downstream from reference 1 and 4007.1 ft upstream from reference 2. The feature is located 24.3 ft downstream from the reference girth weld.

As shown in Table I, line 1, the pipeline SCC wall data was graded (shortlisted) to have crack-like features (column G). The feature in line 1 was further graded to have characteristics of a most crack-like feature (column F). The location of this pipeline SCC wall crack-like feature was also confirmed by low level external metal loss data, shown in columns H, I and J of Table I. As shown in column H of Table I, the low level external metal loss data matched the location of the pipeline crack-like feature at a longitudinal distance of about 4.0 inches and a radial orientation of about 1.0 hour, based on 12 hour clock scale. This pipeline wall crack-like feature was also located in the pipeline body wall near low level external metal loss located at a longitudinal distance of about 20.0 inches and a radial orientation of about 2.0 hour, based on 12 hour clock scale. Additionally, another crack-like shortlisted feature shown in line 3 was confirmed as being located in the same pipe joint where other low level metal loss was indicated to be present, as shown in column J of Table I. The soil characterization data, shown in column K of Table I, confirm that such conditions were conducive for SCC.

Similar results were obtained for the pipeline inspections shown at line 27 of Table I. At this inspection location, the pipeline wall was confirmed to contain low level external metal loss and SCC susceptible soil characterization. In this example, and using the method of this invention, an in-line smart tool inspection showing over two thousand crack-like reflector features was reduced to 12 pipe segment locations by comparing the results with low level metal loss inspection data, taking into consideration whether they could be long seam welding manufacturing defects. When soil characterization data was considered, the number of pipe joint segments that were predicted as having SCC was reduced to 4.

EXAMPLE 2

Near neutral/low pH stress corrosion cracking rupture recently occurred on a 30" high-pressure gas pipeline. Previously, a digital in-line inspection metal loss survey had been performed and the survey was graded using traditional interpretation standards beginning grading at 15% penetration in pipe body wall depth.

To determine the extent of near neutral/low pH stress corrosion cracking on adjacent pipe, a low level external corrosion analysis was performed on the survey above for a section of pipeline located 2,039 feet upstream and downstream from the SCC rupture site. By then examining the low level external corrosion patterns where the stress corrosion cracking failure occurred, several sites were determined to have the same metal loss pattern characteristics as the rupture area. Five separate location pipeline excavations were performed within the 2,039 feet section of pipeline graded for low level external corrosion. This area had already been confirmed as susceptible to environmental stress corrosion cracking as a result of the SCC rupture. Stress corrosion cracking was confirmed to exist on the pipeline at the five separate excavation sites. These sites were excavated and physically examined to confirm the presence of SCC and all SCC was cataloged for location on the pipeline, such as the radial orientation (o'clock position), the longitudinal distance (linear distance) and SCC crack dimensional analysis.

A soil characterization model survey and a pipeline stress corrosion cracking smart tool in-line inspection survey were performed on the ruptured pipeline section. The preliminary smart tool data confirmed the presence and location of serious stress corrosion cracks-like features already cataloged in the five excavations adjacent to the SCC failure site. At this time, preliminary soil characterization data also matched the SCC locations identified and cataloged above. Additional pipe was exposed to confirm the presence of SCC at locations matched by all three data sources—soil characterization, low level external corrosion, and SCC smart tool results.

Additional preliminary stress corrosion cracking feature locations approximately five miles north of the pipeline rupture site were also excavated and examined for SCC. The preliminary soil characterization survey data confirmed the locations as susceptible to near neutral/low pH stress corrosion cracking. Low level external corrosion analysis was performed on the same physical pipe joint locations identified as containing serious stress corrosion cracks. It was confirmed that low level external corrosion matched locations on pipe joints requested for analysis where SCC anomaly features were reported. Additionally, three separate excavations and pipe examinations were performed to confirm the existence of serious SCC requiring pipe removal and replacement. The graded low level external corrosion analysis confirmed shallow external corrosion pitting at these SCC anomaly feature locations.

This invention has several advantages over prior art methods. The combination of these existing technologies and empirical evaluations of such technologies, when used together, yield very high confidence to interpretation of where SCC does and does not exist. Traditional detection methods for near neutral/low pH stress corrosion cracking anomalies on pipelines have proven to be very costly to mitigate due to many false indications of SCC. This invention allows detection with high confidence that actual SCC exists where indicated.

The foregoing description of a preferred embodiment of the invention has been presented for purposed of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined by the claims set forth below.

TABLE I

| Line Number | Inspection Location A | Girth Weld Number B | Absolute Distance (feet) C | Relative Longitudinal Distance D | Inspection Orientation (hrs:mins) E | SCC/EW Reflectors Data Shortlisted Most Crack-like F | SCC/EW Reflectors Data Shortlisted G | Low Level External Metal Loss Data Match with Pipeline Wall Data ±4 in. (Long. Dist.) & ±1 hrs. (Orient.) H | Low Level External Metal Loss Data Match with Pipeline Wall Data ±20 in. (Long. Dist.) & ±2 hrs. (Orient.) I | Same Pipe Joint J | Soil Data K |
|---|---|---|---|---|---|---|---|---|---|---|---|
| 1 | Pipe Body | 28600 | 99481.2 | 24.2 | 5:42 | √ | √ | √ | √ | √ | AL1 |
| 2 | Pipe Body | 28600 | 99482.7 | 25.8 | 9:50 | | | | √ | √ | AL1 |
| 3 | Pipe Body | 28600 | 99484.2 | 27.3 | 9:08 | | √ | | √ | √ | AL1 |
| 4 | Pipe Body | 28600 | 99484.9 | 28.0 | 8:40 | | | | √ | √ | AL1 |
| 5 | Pipe Body | 28620 | 99520.9 | 5.9 | 3:09 | | | | √ | √ | AL1 |
| 6 | Pipe Body | 28620 | 99521.7 | 6.7 | 4:41 | | | | √ | √ | AL1 |
| 7 | Pipe Body | 28620 | 99527.1 | 12.2 | 4:33 | | | | √ | √ | AL1 |
| 8 | Pipe Body | 28700 | 99757.3 | 5.8 | 10:58 | | √ | | | √ | AL1 |

TABLE I-continued

| | | | | | | SCC/EW Reflectors Data | | Low Level External Metal Loss Data Match with Pipeline Wall Data | | | |
|---|---|---|---|---|---|---|---|---|---|---|---|
| Line Number | Inspection Location A | Girth Weld Number B | Absolute Distance (feet) C | Relative Longitudinal Distance D | Inspection Orientation (hrs:mins) E | Shortlisted Most Crack-like F | Shortlisted G | ±4 in. (Long. Dist.) & ±1 hrs. (Orient.) H | ±20 in. (Long. Dist.) & ±2 hrs. (Orient.) I | Same Pipe Joint J | Soil Data K |
| 9 | Pipe Body | 28700 | 99774.4 | 22.9 | 9:04 | | | | | √ | AL1 |
| 10 | Pipe Body | 28720 | 99811.3 | 15.3 | 12:22 | | | | | | AL1 |
| 11 | Pipe Body | 28800 | 100039.6 | 2.8 | 7:45 | | | | | | AL2 |
| 12 | Pipe Body | 28800 | 100060.1 | 23.2 | 9:39 | | | | | | AL2 |
| 13 | Pipe Body | 28800 | 100062.3 | 25.5 | 7:59 | | √ | | | | AL2 |
| 14 | Pipe Body | 28800 | 100062.3 | 25.5 | 10:14 | | | | | | AL2 |
| 15 | Pipe Body | 28800 | 100063.1 | 26.2 | 8:43 | | | | | | AL2 |
| 16 | Pipe Body | 28800 | 100064.5 | 27.7 | 4:26 | | √ | | | | AL2 |
| 17 | Pipe Body | 28800 | 100064.8 | 28.0 | 10:48 | | √ | | | | AL2 |
| 18 | Pipe Body | 28800 | 100065.3 | 28.5 | 8:38 | | | | | | AL2 |
| 19 | Pipe Body | 28800 | 100065.5 | 28.7 | 6:55 | | | | | | AL2 |
| 20 | Pipe Body | 28840 | 100168.6 | 10.2 | 9:50 | | | | | | AL2 |
| 21 | Pipe Body | 28840 | 100172.5 | 14.0 | 9:11 | | | | | | AL2 |
| 22 | Pipe Body | 28840 | 100174.5 | 16.1 | 6:43 | | | | | | AL2 |
| 23 | Pipe Body | 28840 | 100177.5 | 19.1 | 9:03 | | | | | | AL2 |
| 24 | Pipe Body | 28850 | 100196.8 | 7.2 | 7:10 | | | | | | AL2 |
| 25 | Pipe Body | 28880 | 100280.7 | 1.5 | 7:26 | | | | | | AL2 |
| 26 | Pipe Body | 28900 | 100344.8 | 4.4 | 8:34 | | | | √ | √ | AL2 |
| 27 | Pipe Body | 28900 | 100357.9 | 17.4 | 8:28 | | √ | | √ | √ | AL2 |
| 28 | Pipe Body | 28900 | 100362.7 | 22.2 | 9:35 | | | | √ | √ | AL2 |
| 29 | Pipe Body | 28900 | 100365.0 | 24.5 | 4:35 | | | | √ | √ | AL2 |
| 30 | Pipe Body | 28900 | 100365.8 | 25.3 | 9:37 | | | | √ | √ | AL2 |
| 31 | Pipe Body | 29220 | 101295.2 | 0.9 | 7:45 | | | | | | AL1 |
| 32 | Pipe Body | 29220 | 101297.3 | 3.0 | 7:14 | | √ | | | | AL1 |

That claimed is:

1. A method of determining crack locations associated with a tubular member, the method comprising:
   locating a set of stress corrosion cracking indicators associated with a tubular member;
   locating a set of low-level corrosion indicators associated with a tubular member;
   comparing locations of the set of stress corrosion cracking indicators with locations of the set of low-level corrosion indicators;
   establishing a subset of stress corrosion cracking indicators and a subset of low-level corrosion indicators when the location of any of the set of stress corrosion cracking indicators is located within a first preselected distance from any of the set of low-level corrosion indicators;
   locating a set of soil characterization indicators associated with the tubular member;
   comparing locations of the set of soil characterization indicators with locations of the subset of stress corrosion cracking indicators and locations of the subset of low-level corrosion indicators;
   establishing a plurality of predictor stress corrosion cracking indicators, a plurality of predictor low-level corrosion indicators, and a plurality of predictor soil characterization indicators when the location of any of the set of soil characterization indicators is located both within a second preselected distance from any of the subset of stress corrosion cracking indicators and within a third preselected distance from any of the subset of low-level corrosion indicators; and
   predicting at least one of a plurality of locations associated with the tubular member susceptible to stress corrosion cracking responsive to at least two of the plurality of predictor indicators.

2. A method as defined in claim 1, wherein the set of stress corrosion cracking indicators comprise a crack-like feature associated with the tubular member, wherein the set of low-level corrosion indicators comprise a low-level metal loss feature associated with the tubular member, wherein the set of soil characterization indicators comprise characteristics selected from the group consisting of: chemical content, pH level, and terrain elevation, and wherein the step of predicting includes selecting the locations having a high probability of the presence of stress corrosion cracking associated with the tubular member thereby minimizing false impressions of stress corrosion cracking due to anomalies associated with the tubular member.

3. A method as defined in claim 2, further comprising the step of evaluating the tubular member to gather data relating to the tubular member, wherein the evaluating includes using tools selected from the group consisting of: elastic wave, electro-magnetic acoustic, and digital magnetic flux leakage, and wherein a first, second, and third preselected distance each comprises directional components of both a preselected longitudinal distance and a preselected radial distance.

4. A method of determining crack locations associated with a tubular member, the method comprising:
   evaluating the tubular member to gather data relating associated with the tubular member;
   locating a plurality of stress corrosion cracking indicators associated with the tubular member;
   locating a plurality of low-level corrosion indicators associated with the tubular member;
   locating a plurality of soil characterization indicators associated with the tubular member;
   establishing a plurality of predictor stress corrosion cracking indicators, a plurality of predictor low-level corrosion indicators, and a plurality of predictor soil characterization indicators when any of the plurality of stress corrosion cracking indicators, any of the plurality of low-level corrosion indicators and any of the plurality of soil characterization indicators are located within a preselected distance from each other; and predicting a plurality of locations on the tubular member susceptible to stress corrosion cracking responsive to at least two of the plurality of predictor indicators.

5. A method as defined in claim 4, wherein the predicting indicates a high probability of the presence of stress corrosion cracking associated with the tubular member thereby minimizing false impressions of stress corrosion cracking due to manufacturing or construction anomalies on the tubular member.

6. A method as defined in claim 4, wherein the stress corrosion cracking indicators comprise a crack-like feature associated with the tubular member, wherein the low-level corrosion indicators comprise a low-level metal loss feature associated with the tubular member, and wherein the soil characterization indicators comprise characteristics selected from the group consisting of: chemical content, pH level, and terrain elevation.

7. A method as defined in claim 4, wherein preselected distance comprises directional components of both a preselected longitudinal distance and a preselected radial distance.

8. A method as defined in claim 7, wherein the preselected longitudinal distance is within 4 inches and the preselected radial orientation.

9. A method as defined in claim 7, wherein the preselected longitudinal distance is within 20 inches and the preselected radial orientation.

10. A method as defined in claim 4, wherein the evaluating includes using tools selected from the group consisting of: elastic wave technology, electro-magnetic acoustic technology, and digital magnetic flux leakage technology.

11. A system to determine crack locations on a tubular member, the system comprising:

a comparator to compare locations of a set of stress corrosion cracking indicators associated with a tubular member with locations of a set of low-level corrosion indicators associated with the tubular member to thereby establish a subset of stress corrosion cracking indicators and a subset of low-level corrosion indicators, responsive to comparing the sets of indicators, when the location of any of the set of stress corrosion cracking indicators is located within a first preselected distance from any of the set of low-level corrosion indicators, the comparator further comparing locations of a set of soil characterization indicators associated with the tubular member with locations of the subset of stress corrosion cracking indicators and locations of the subset of low-level corrosion indicators; and a predictor to predict that a segment of the tubular member is susceptible to stress corrosion cracking, responsive to comparing the set of soil characterization indicators with the subsets of indicators, when any of the set of soil characterization indicators is located both within a second preselected distance from any of the subset of stress corrosion cracking indicators and within a third preselected distance from any of the subset of low-level corrosion indicators.

12. A system as defined in claim 11, wherein the predictor indicates a high probability of the susceptibility of stress corrosion cracking associated with the tubular member thereby minimizing false impressions of stress corrosion cracking due to manufacturing or construction anomalies associated with the tubular member.

13. A system as defined in claim 11, wherein the stress corrosion cracking indicators comprise a crack-like feature associated with the tubular member, and wherein the low-level corrosion indicators comprise a low-level metal loss feature associated with the tubular member, wherein the soil characterization indicators comprise characteristics selected from the group consisting of: chemical content, pH level, and terrain elevation.

14. A system as defined in claim 13, wherein preselected distance comprises directional components of both a preselected longitudinal distance and a preselected radial distance.

15. A system as defined in claim 14, wherein the preselected longitudinal distance is within 4 inches and the preselected.

16. A system as defined in claim 14, wherein the preselected longitudinal distance is within 20 inches and the preselected.

17. A system as defined in claim 14, wherein the system includes at least one tool selected from the group consisting of: elastic wave, electro-magnetic acoustic, and digital magnetic flux leakage.

18. A system to determine crack locations associated with a tubular member, the system comprising:

a comparator to compare locations of a set of stress corrosion cracking indicators associated with the tubular member with locations of a set of low-level corrosion indicators associated with the tubular member to thereby establish a subset of stress corrosion cracking indicators and a subset of low-level corrosion indicators, responsive to comparing the sets of indicators, when the location of any of the set of stress corrosion cracking indicators is located within a first preselected distance from any of the set of low-level corrosion indicators, the comparator also being positioned to compare locations of a set of soil characterization indicators associated with the tubular member with locations of the subset of stress corrosion cracking indicators and locations of the subset of low-level corrosion indicators; and a confirmer to confirm a presence of stress corrosion cracking in a segment of the tubular member, responsive to comparing the set of soil characterization indicators with the subsets of indicators, when any of the set of soil characterization indicators is located both within a second preselected distance from any of the subset of stress corrosion cracking indicators and within a third preselected distance from any of the subset of low-level corrosion indicators.

19. A system as defined in claim 18, wherein the confirmer also indicates a high probability of the presence of stress corrosion cracking in the tubular member thereby minimizing false impressions of stress corrosion cracking due to manufacturing or construction anomalies on the tubular member.

20. A system as defined in claim 18, wherein the stress corrosion cracking indicators comprise a crack-like feature associated with the tubular member, wherein the low-level corrosion indicators comprise a low-level metal loss feature associated with the tubular member, and wherein the soil characterization indicators comprise characteristics selected from the group consisting of: chemical content, pH level, and terrain elevation.

21. A system as defined in claim 18, wherein preselected distance comprises directional components of both a preselected longitudinal distance and a preselected radial distance.

22. A system as defined in claim 21, wherein the preselected longitudinal distance is within 20 inches and the preselected radial distance is within 60 degrees.

23. A system as defined in claim 18, wherein the indicators of the system are determined at least one using tool selected from the group consisting of: elastic wave, electromagnetic acoustic, and digital magnetic flux leakage.

24. A method of determining crack locations associated with a pipeline body wall, the method comprising:
- detecting a set of crack-like features associated with the pipeline;
- detecting a set of low-level metal loss corrosions;
- comparing locations of the set of crack-like features with locations of the set of low-level metal loss corrosions;
- establishing a subset of crack-like features and a subset of low-level metal loss corrosions, responsive to comparing the set of crack-like features with the set of low-level metal loss corrosions, when the location of any of the set of crack-like features is located within a first preselected distance from any of the set of low-level metal loss corrosions;
- detecting a set of soil characterization models;
- comparing locations of the set of soil characterization models with locations of the subset of crack-like features and locations of the subset of low-level metal loss corrosions; and
- confirming with high probability the presence of stress corrosion cracks associated with the pipeline body wall when the location of any of the set of soil characterization models is located both within a second preselected distance from any of the subset of crack-like features and within a third preselected distance from any of the subset of low-level metal loss corrosions.

25. A method of predicting a location of stress crack corrosion in a gas pipeline, the method comprising:
- integrating in-line pipeline wall inspection results, in-line low level external metal loss, external corrosion analysis results, and soil characterization model results; and
- comparatively evaluating the in-line pipeline wall inspection results, the in-line low level external metal loss, the external corrosion analysis results, and the soil characterization model results to determine with a high confidence level whether actual stress corrosion cracking exists at a physical gas pipeline segment location responsive to the integrating.

* * * * *